(12) United States Patent
Chiwanga et al.

(10) Patent No.: US 7,351,220 B2
(45) Date of Patent: Apr. 1, 2008

(54) PORTABLE DEVICE FOR DELIVERING MEDICAMENTS AND THE LIKE

(75) Inventors: States Gwinyai Chiwanga, Dullingham (GB); Terence George Fielder, Nottingham (GB); Andrew Robert Fry, Barnet (GB)

(73) Assignee: Team Holdings (UK) Limited, Barkway (GB)

( * ) Notice: Subject to any disclaimer, the term of this patent is extended or adjusted under 35 U.S.C. 154(b) by 700 days.

(21) Appl. No.: 10/048,294

(22) PCT Filed: May 21, 2001

(86) PCT No.: PCT/GB01/02227

§ 371 (c)(1),
(2), (4) Date: May 12, 2003

(87) PCT Pub. No.: WO01/89612

PCT Pub. Date: Nov. 29, 2001

(65) Prior Publication Data

US 2003/0176839 A1 Sep. 18, 2003

(30) Foreign Application Priority Data

May 20, 2000 (GB) .................................. 0012165.7

(51) Int. Cl.
*A61M 5/30* (2006.01)
*A61M 1/00* (2006.01)

(52) U.S. Cl. ........................................ 604/69; 604/152

(58) Field of Classification Search ............ 604/68–72, 604/141, 131, 140, 147, 187, 143, 145, 151, 604/152
See application file for complete search history.

(56) References Cited

U.S. PATENT DOCUMENTS

| 4,059,107 A | * | 11/1977 | Iriguchi et al. ............... 604/71 |
| 4,089,334 A | * | 5/1978 | Schwebel et al. ............ 604/69 |
| 5,860,957 A | | 1/1999 | Jacobsen |
| 6,045,534 A | * | 4/2000 | Jacobsen et al. ............ 604/156 |

FOREIGN PATENT DOCUMENTS

EP 0 316 468 A2 5/1989

* cited by examiner

*Primary Examiner*—Matthew F. DeSanto
(74) *Attorney, Agent, or Firm*—Barnes & Thornburg LLP

(57) ABSTRACT

Disclosed is a portable device for delivering a medicament or the like into the body of a human or animal subject, the device comprising: a medicament compartment containing the medicament or the like to be delivered; delivery means comprising an orifice through which the medicament or the like is expelled from the device; and an internal combustion engine which provides the motive force by which the medicament is expelled from the device.

16 Claims, 3 Drawing Sheets

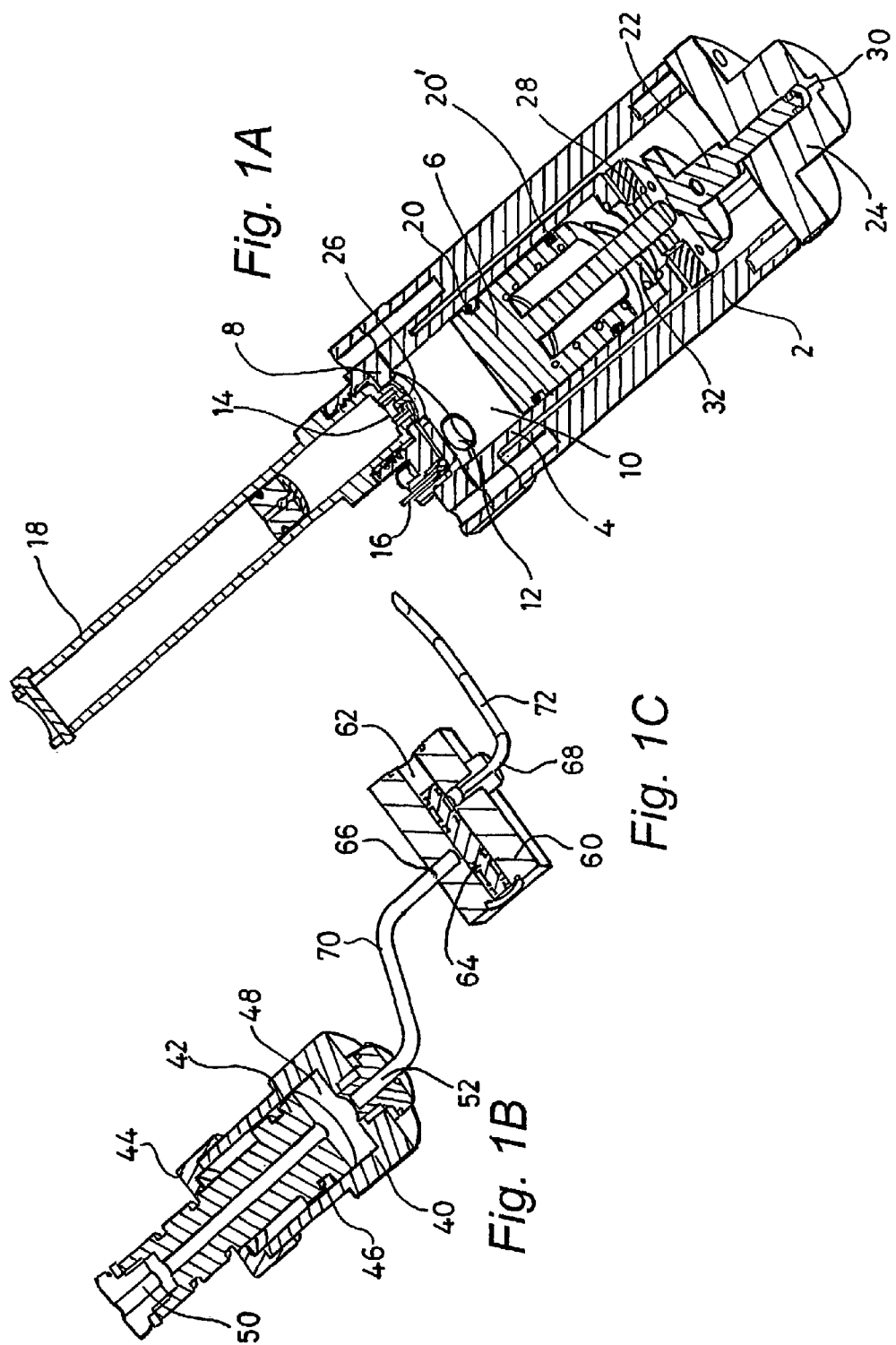

PORTABLE DEVICE FOR DELIVERING MEDICAMENTS AND THE LIKE

FIELD OF THE INVENTION

This invention relates to a portable device for delivering medicaments and the like.

BACKGROUND OF THE INVENTION

The internal combustion engine and its principles of operation are of course well-known. It is also known to produce a portable tool with a small internal combustion engine. Such a tool, for fixing fasteners to a workpiece, is disclosed in EP 0 316 468, U.S. Pat. No. 4,483,474 and U.S. Pat. No. 4,522,162.

EP 0 316 468 describes in detail the construction and operation of a fastener tool equipped with a combustion chamber, into which is introduced a fuel/air mixture, combustion of which (ignited by a spark) drives a piston/working member assembly. However this arrangement is such that the power output tends to vary from one combustive cycle to the next, within quite wide limits. This deficiency is not a serious problem for power tools of the type disclosed in the prior art, since the device can be designed such that the likely minimum power output of any single combustive event is above the maximum required to perform the desired activity (e.g. driving fasteners into a workpiece) with any excess kinetic energy being absorbed by the rigid surface of the workpiece. However, in other applications, such a solution is not feasible or desirable.

SUMMARY OF THE INVENTION

In a first aspect the invention provides a portable device for delivering a medicament or the like into the body of a human or animal subject, the device comprising: a medicament compartment containing the medicament or the like to be delivered; delivery means comprising an orifice through which the medicament or the like is expelled from the device; and an internal combustion engine which provides the motive force by which the medicament is expelled from the device.

The term "medicament" as used herein is intended to encompass any substance which may be administered to a human or animal body for beneficial purposes and includes, but is not limited to, conventional pharmaceutical preparations (such as antibiotics, steroids, non-steroidal anti-inflammatory drugs, analgesics, anaesthetics etc.), vaccine compositions, and vitamin and/or mineral preparations. The medicament may be a liquid (e.g. solution or suspension) or in any other form.

It will be appreciated that the portable device of the invention is, in essence, a hand-held injector. The injector device may be associated with a hypodermic needle, which is inserted into the subject's body. In preferred embodiments however, the injector will be a needleless injector, in which penetration of the subject's body is achieved by expelling the medicament from the injector at a sufficiently high velocity. The device may be used to make injections transdermally (including sub-cutaneous and intra-muscular injections), intradermally, and also to inject at mucosal surfaces (e.g. the gums).

As far as the inventors are aware, there has never been any previous suggestion that an internal combustion engine can be used to provide the motive force to expel a medicament from a portable injector device for delivering a medicament to a subject. Indeed there are many reasons why the selection of an internal combustion engine to provide the motive force would not have been considered by the person skilled in the art of designing medicament delivery devices since most internal combustion engines are rather large, and heavy, and so are difficult to scale down to fit within a portable device.

Whilst internal combustion engines have been used to provide the power source of portable power tools, such uses are very far removed from injection of medicaments and would not have been considered as a relevant technical field by those skilled in the art of injector devices. For example, an injector device has to be capable of delivering small doses of medicament (e.g. as small as 100 µl or so) very accurately and reproducibly. In contrast, no such accuracy and reproducibility is required from a power tool. Thus, for instance, for a needleless injector the power output of the internal combustion engine must be precisely controlled, since if the power output is too low the medicament may fail to penetrate the subject's body and if the power output is too high the medicament may penetrate the subject's body more deeply than desired. In addition, a fairly high noise volume associated with operation of the device is acceptable with a power tool, but is completely unacceptable for an injector, especially if the device is being used to administer a medicament to livestock or other animals which would be unsettled by loud noise.

It will be apparent that certain features of the device are implicit as a result of the presence of the internal combustion engine. In a typical embodiment the portable device of the invention will comprise: a body or housing comprising a cylinder, a piston located within the cylinder, and a cylinder head; a combustion chamber defined by the cylinder head, the cylinder and the piston, the combustion chamber being provided with means for forming a combustible mixture of fuel and combustion-supporting gas in the chamber and ignition means for igniting the mixture; and a work member operably linked (but not necessarily attached) to the piston.

The combustion-supporting gas may be oxygen or other gas comprising oxygen. Conveniently the combustion-supporting gas will be air.

The device as a whole is of such dimensions as to be readily hand-held in use, and preferably small enough to fit in trouser or jacket pocket of average size. The body or housing is preferably formed from heat-resistant plastics material or metal (e.g. steel). The cylinder, cylinder head and piston may conveniently be formed of metal (e.g. steel or the like), ceramics, composite or plastics materials. The means for forming a combustible mixture of fuel and air or other combustion-supporting gas in the combustion chamber will generally comprise a fuel inlet and a separate air inlet. One or both of these inlets may conveniently be provided with valve means to regulate the flow of fuel or air, as the case may be.

The fuel is advantageously one which is gaseous at atmospheric pressure (760 mm Hg) and room temperature (20° C.) but which can be caused to liquefy at room temperature by mildly elevated pressure. Examples of suitable fuels include butane (which is commonly used as a fuel in disposable cigarette lighters) and propane. Desirably therefore the fuel is held as a liquid, under pressure, in a fuel reservoir.

In preferred embodiments of the invention the device provides a substantially consistent power output from one combustive event to the next. In order to achieve this desired objective, it is necessary to ensure that a consistent amount of fuel is present in the combustion chamber for each combustive event. Accordingly, in preferred embodiments, the device comprises means for introducing an accurately pre-determined amount of fuel into the combustion chamber for each combustive event.

Accordingly, in a preferred embodiment the device of the invention comprises a fuel dosing assembly for metering a dose of fuel from a reservoir of liquefied gas fuel to be delivered to the combustion chamber, wherein the dose of liquefied gas fuel is accurately metered without undergoing a partial phase change.

By way of explanation liquefied fuels such as propane and butane tend to vaporise as soon as they are removed from the elevated pressure under which they are stored. The inventors found that this phase change rendered it extremely difficult to meter an accurate dose of fuel consistently. Accordingly, in preferred embodiments it is desired that a liquefied gaseous fuel is measured and dosed whilst still under pressure (and thus in liquid form), which allows for far greater consistency of fuel dosing. The inventors have devised a number of fuel dosing assemblies consistent with this preferred feature, at least one of which is described in detail below. Conveniently the fuel dosing assembly comprises a spool valve or a rotary valve.

In devices of the sort disclosed in EP 0 316 468, at least a partial phase change of the fuel can take place in the fuel dosing assembly, especially once the fuel reservoir becomes less than half filled with liquefied gas fuel. In the prior art arrangement, when the reservoir is full and the first doses of fuel are used, small amounts of liquid gas fuel vaporise, and the resulting vapour pressure serves to maintain the pressure in the fuel reservoir, and thus keep the rest of the fuel in liquid form. This 'passive' pressurisation becomes increasingly less efficient as more and more fuel is used.

In contrast, in preferred embodiments of the device of the invention, the fuel reservoir is 'actively' pressurised, at a substantially constant pressure, which is effective in keeping all of the fuel in the reservoir in liquid form. Such active pressurising means may comprise, for example, a spring means acting on a movable pressure plate or piston within the fuel reservoir.

In order to optimise the consistency of power output of the engine, it is desirable that the device will comprise priming means for introducing an accurately pre-determined amount of oxygen, air, or other combustion-supporting gas, into the combustion chamber before each combustive event. In particular (but not essentially) it is desirable that the device of the invention includes both a priming means for introducing an accurately pre-determined amount of oxygen or air etc, and a fuel dosing means (as described above) for introducing an accurately predetermined amount of fuel, into the combustion chamber prior to each combustive event.

Desirably the device comprises means for causing compression of the combustion-supporting gas within the combustion chamber prior to combustion. More particularly the device will conveniently comprise means for causing compression of the fuel/combustion-supporting gas mixture within the combustion chamber. Conveniently operation of the priming means will not only introduce the combustion-supporting gas into the combustion chamber, but also will directly or indirectly cause compression of the gas (or gas/fuel mixture). Where the combustion-supporting gas is air, the gas will desirably be compressed above the ambient atmospheric pressure.

Any priming means capable of introducing the combustion-supporting gas into the combustion chamber (and, optionally, compressing the gas) may be usefully employed.

In one embodiment, described in detail below, the priming means comprises a manually-operated plunger, with a fixed travel, within a priming cylinder. Pulling the plunger upwards to the top of its fixed travel introduces a fixed volume of air into the priming means. Depression of the plunger, to the bottom of its fixed travel, forces open the air inlet into the combustion chamber and compresses the air within the chamber, which is held in compression by the one-way action of an inlet valve. The amount of air introduced into the chamber may simply be varied by altering the number of strokes of the plunger. In an alternative embodiment, the piston which in part defines the combustion chamber, may additionally be used to act as the priming means, such that movement of the piston compresses the air/fuel mixture in the combustion chamber.

For the avoidance of doubt, it should be stated that in preferred embodiments, the amount of fuel and/or air (or other combustion-supporting gas) introduced into the chamber can be altered between predetermined, fixed amounts. Thus, the power output of the device is consistent for a given volume of fuel and air, but these can be adjusted as desired, to increase or decrease the power output of the device between pre-determined set values. Thus, for example, the fuel dosing assembly may be arranged to meter one of several, fixed amounts of fuel. Preferably the fuel and/or air inlets, by which the fuel and air (or other combustion-supporting gas) are respectively introduced into the combustion chamber, will be shaped so as to set up turbulent flow, facilitating mixing of the fuel and air upon entry into the combustion chamber.

It will be apparent that in those embodiments a device in accordance the invention defined above, in which the combustion chamber is pressurised prior to ignition of the air/fuel mixture, such superatmospheric pressure would tend to displace the piston downwards. In order to resist this the device preferably comprises a restraining means, acting directly or indirectly on the piston, which serves to keep the piston in place against the pressure of the compressed air/fuel mixture, but which is insufficient to restrain the piston when the air/fuel mixture is ignited. In one embodiment the device is provided with one or more spring-biased fingers, typically mounted or acting generally perpendicular to the direction of travel of the piston, which fingers engage co-operatively shaped recesses on the piston or working member, the spring-biasing acting to urge the fingers into engagement with and thereby restrain, the piston or working member. In an alternative embodiment the restraining member takes the form of a resiliently-deformable, or a rupturable, retaining device. An example of a rupturable retaining device is a shear pin, or similar, which can secure the piston (or work member). In another embodiment the restraining means comprises one or more struts spring-biased or resiliently deformable, so as to be displaceable, mounted generally parallel to the direction of travel of the piston, but with an angled surface at the upper end proximal to the piston, the strut or struts being displaceable outwards by the piston upon combustion.

The ignition means conveniently takes the form of a spark plug. This may be powered by a piezoelectric ignition circuit e.g. of the type disclosed in EP 0316468. In preferred embodiments the ignition means will be interlocked such that it is inoperable unless the rest of the device is in a primed state ready to fire. A her preferred feature is that the ignition means can be disabled as soon as combustion has commenced, in order to conserve electrical energy. It may also be desired to limit the electrical output of the ignition means to below the breakdown voltage of the spark gap, and then initiate spark formation in a controlled manner. Controlled ignition may be achieved, for example, by means of a pulse transformer (as used in electronic flash apparatus) or by means of a piezoelectric spark generator, itself insufficient to cause ignition but capable of opening an ionization path for the main spark to follow.

A device in accordance with the invention will generally comprise one or more further components associated with a conventional internal combustion engine. In particular, the device will conveniently comprise an exhaust outlet to allow the products of combustion to exit the combustion chamber.

The device may be used to deliver a medicament to a human subject or to any animal subject, including birds (especially poultry), farm livestock (such as sheep, pigs, cattle, goats, horses), and companion animals (especially cats and dogs). It is desirable to minimise the noise of operation of the injection device to avoid discomfort or irritation to the recipient of the medicament, and any nearby people or animals. The inventors have noted that, in this respect, it is desirable that the residual energy of the products of combustion is at least largely dissipated before the exhaust valve is opened, so that venting of the cylinder following combustion is accomplished quietly.

Preferably the exhaust valve is closed throughout the induction, compression, ignition and power delivery phases of the operating sequence and the exhaust valve opens only once the combustion has been completed and all movement (downstroke or upstroke) of the piston ceased. In one embodiment this is achieved as part of a manual operating sequence, and may typically be the penultimate step of the sequence prior to resetting the piston, ready for storage of the device until, it is to be used again. Alternatively, the exhaust valve may be opened automatically (e.g. a determined length of time after ignition). In either event it is preferred that a locking mechanism prevents premature opening of the exhaust valve.

The device will also further advantageously comprise return means, to return the piston to a primed position when the device has been fired. The return means may comprise a simple spring biasing means, such as a compression spring mounted in a lower portion of the body of the device, which spring is compressed by the stroke of the piston such that, when the force on the piston from the compressed spring is greater than the force exerted by the gaseous post-combustion products, the piston will tend to return to its primed position. Alternatively, or additionally, the depression of the piston can be used to compress gas in a compartment beneath the piston, thus leading to an increase in pressure acting upwards on the piston which, when it becomes greater than the downward pressure of the combustion products acting on the piston, will tend to return the piston to its primed position. An arrangement incorporating both of these features is disclosed in EP 0 316 468.

Preferably the device of the invention will include each of the following features: (a) means for causing compression of the fuel/air (or other combustion-supporting gas) mixture prior to combustion; (b) restraining means, serving to keep the piston in place (prior to combustion) against the pressure of the compressed fuel/air mixture; and (c) return means, to return the piston to the primed position when the device has been fired. Advantageously the restraining means (b) and the return means (c) are provided by separate components.

Desirably the return means is weak, being only just sufficient to overcome the inherent resistance of the piston, typically when the pressure above the piston is equal to or less than ambient pressure and/or when the exhaust valve has been opened.

The work member typically takes the form of a metallic (e.g. steel) piston rod or push rod welded, screw-threaded or otherwise operably linked with the piston. It should be noted that it is not essential for the work member to be rigidly attached, or physically connected, to the piston. For example, the operable linkage between the piston and the work-member could take the form of a hydraulic fluid-filled conduit, the hydraulic fluid in the conduit serving to transfer energy from the piston to the work member. In such an arrangement the piston never comes into physical contact with the work member. However, a more preferred arrangement provides a temporary separation between the piston and the work member (e.g. a small, air-filled gap)—the piston initially being separated from the work member when the device is primed, which separation allows the piston to reach a higher velocity (following combustion) before contacting the work member. Accordingly, greater initial acceleration is conferred on the work member than would have occurred if the piston was in physical contact (or otherwise rigidly-linked) with the work member at all times.

It is particularly envisaged that the device of the invention may be used as an auto-injector (i.e. the subject may use the device to administer a substance to his or her own body), with or without a needle, because the device is easy to use (requiring very little force to operate the priming means) and requires no medical training or expertise to operate accurately.

As may be appreciated, the intended application of the device will affect the design such that, for some applications the device may have a set of preferred characteristics which, in another application may be unfeasible or at least undesirable.

It will normally be preferred that the device of the invention will perform only a single combustive event when the trigger is actuated so as to avoid, for instance, inadvertent repeated injection of a subject. Such a device may be described as "single shot" in that it requires re-priming before it will fire again. This may require manual re-priming by the user or may be effected automatically. It will, however, be preferred that the device is provided with sufficient reserves of fuel and (if appropriate) electrical energy that it will be capable of performing a plurality (e.g. 1000 or 2000) firing cycles before the fuel and/or electrical energy reserves (if present) are exhausted.

The medicament chamber of the device may contain sufficient medicament for just a single dose for delivery to the subject, so as to require replenishment with medicament after delivery of each dose of medicament. Alternatively, the medicament chamber may contain sufficient medicament for a plurality of doses, such that only occasional replenishment is required. In the latter situation, the medicament chamber will conveniently be provided or associated with dosing means, such that an appropriately-sized, measured dose of medicament is delivered each time the device is used. Desirably the dosing means is adjustable between different positions so that various pre-determined doses of medicament may be delivered. Appropriate dosing means are familiar to those skilled in the art.

The medicament chamber may form an integral part of the device of the invention, or may take the form of a readily removable component.

Needleless injectors per se are well known to those skilled in the art. Examples of such devices include those disclosed by Schwebel et al, which are powered by a pyrotechnic charge (see U.S. Pat. No. 3,802,430; U.S. Pat. No. 4,089,334 and U.S. Pat. No. 4,124,024).

It is desirable that devices such as needleless injectors have a consistent power output: whilst, on one hand, sufficient power must be provided to force the medicament or other substance through the skin, it is necessary to avoid the use of too much power, otherwise the substance may be injected deeper than is required and may cause greater disruption to the tissues (especially blood vessels) of the subject than is required, leading to extensive and unsightly bruising, and cause pain.

Those skilled in the art will be acquainted with the types and doses of substances which are deliverable by a needleless injector. A typical dose volume will be between 0.01 ml and 2.0 ml. The substance to be delivered may take the form of a liquid (a solution or suspension), but other formulations may be employed.

Ideally, in order to reduce or minimise sensation of pain associated with the injection, the medicament should be administered within an injection interval of less than 500 milliseconds, preferably about 200 milliseconds. Further, in ideal embodiments, there is an initial peak in the injection force provided by the injector in order to overcome the resistance provided by the subject's skin, followed by a longer, sustained force of lower magnitude to deliver the medicament dose. The initial penetrating force is typically in the range 0.4-1.4 Newtons, and the medicament delivery force is advantageously in the range 0.2-0.8 Newtons.

An injection device orifice, through which the medicament is expelled, will conveniently have a diameter in the range 0.1-0.5 mm, more preferably in the range 0.12-0.45 mm. An orifice of these dimensions, with average forces of the magnitude described above, would create an initial medicament velocity of about 120 m/s to penetrate the skin, with the rest of the medicament dose being delivered at a velocity of about 70 m/s. A preferred velocity is in the range 50-150 m/s, which is found suitable for transdermal delivery of most or all of an average dose of medicament to a typical human subject.

In a second aspect the invention provides a method of administering a medicament to a human or animal subject, comprising use of a device as defined above.

The various aspects of the invention will now be described in greater detail by way of illustrative examples and with reference to the accompanying drawings, in which:

FIGS. 1A, 1B and 1C are sectional views (partly cut away) of the isolated components of a portable injector device in accordance with the invention;

DETAILED DESCRIPTION OF AN EMBODIMENT

Figure 2A:
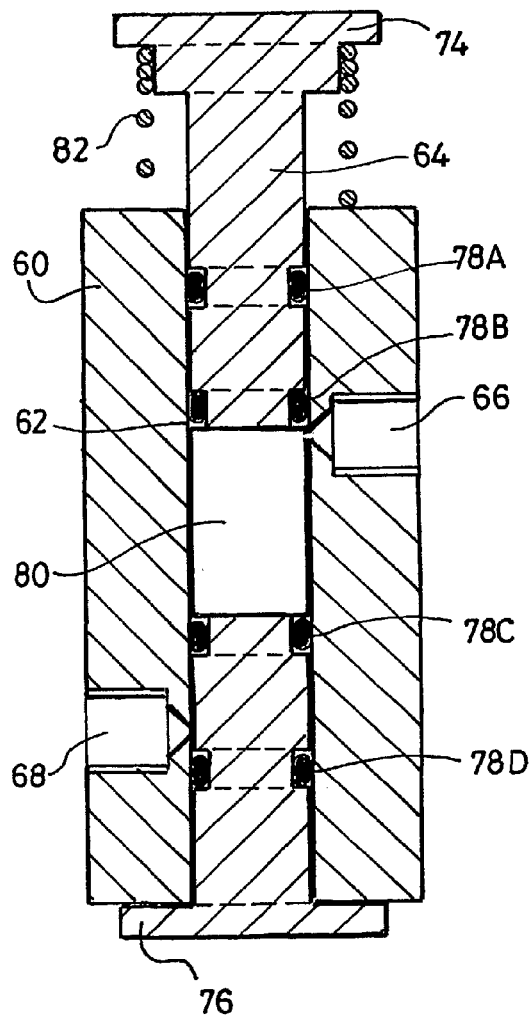
FIGS. 2A and 2B are sectional views, on a different scale, of a fuel dosing assembly for use in a device in accordance with the invention.

FIGS. 1A, 1B and 1C illustrate three components of one embodiment of an injector device in accordance with the invention. The injector comprises a device in accordance with the first and second aspects of the invention. FIG. 1A shows the injector assembly, FIG. 2B shows the fuel reservoir, and FIG. 1C shows the fuel dosing assembly.

Referring to FIG. 1A, an injector assembly comprises a body 2 comprising a cylinder 4, a piston 6 located within the cylinder 4, and a cylinder head 8. A combustion chamber 10 is defined by the inner surfaces of the cylinder 4, piston 6 and cylinder head 8. The combustion chamber 10 is provided with means for forming a combustible fuel/air mixture, comprising fuel inlet (not shown), air inlet 14, and exhaust valve 12. The combustion chamber 10 is also provided with ignition means, comprising spark plug 16.

The injector assembly is additionally provided with priming means 18, which provides for compression of the fuel/air mixture in the combustion chamber 10 prior to combustion. The device is further provided with an electrical power source (rechargeable dry cells) and associated wiring (not shown), to provide electrical power to the spark plug 16 and optionally to auxiliary components such as LED indicator lights to indicate the status (e.g. primed and ready) of the device.

The operation of the embodiment illustrated in the drawings will now be described in detail.

As shown in FIG. 1A, the piston 6 is mounted within the cylinder 4, and sealed by upper and lower O rings (20 and 20' respectively) formed from Viton™ (or other butane-resistant elastomeric material). Both piston 6 and cylinder 4 are formed of steel or aluminium alloy. Piston 6, when ready for firing, is positioned with its lower end close to work member 22 but separated therefrom by a small gap. This small gap is intentionally provided to allow initial acceleration of piston 6 immediately after combustion, prior to contacting the work member 22 (the lower end of which is housed within medicament compartment 24, which comprises a dose of medicament to be delivered when the device is operated). The high velocity achieved by piston 6 before it contacts the upper end of work member 22 causes rapid acceleration thereof upon contact, which is beneficial in causing a pressure impulse to be generated in the medicament chamber 24 and subsequently delivery of medicament through orifice 30. The piston 6 is movable within cylinder 4 from an upper, primed position to a lower, completed stroke position. In FIG. 1A the piston 6 is shown between its upper, primed position and its lower, completed stroke position.

When the piston 6 is in the primed position, an accurately metered dose of fuel is delivered from the fuel reservoir (FIG. 1B) by the fuel dosing assembly (FIG. 1C) as will be described in greater detail below. The fuel passes through a fuel valve (not shown) and enters the combustion chamber 10 via fuel inlet (not shown) in vapour form.

Substantially simultaneously, a predetermined volume of air (and hence an essentially fixed amount of oxygen) is introduced into the chamber 10 from the priming means 18. Air passes from the priming means to the chamber 10 through a Vernay valve 26 seated in the air inlet 14. Again, the priming means will be described in greater detail below.

When the compressed fuel/air mixture is present in the chamber 10 the device is considered primed. The lower end of the medicament compartment 24 is then positioned in contact with the subject at the site where it is delivered to inject the drug. A trigger arrangement (not shown) is then triggered by the user. This causes a voltage to be applied to the spark plug 16, causing a spark to ignite the fuel/air mixture in the chamber 10. The trigger arrangement is conveniently the same or similar to that disclosed in EP 0 316 468.

Initially the piston 6 is held in the primed position, against the pressure of the pressurised fuel/air mixture, by a restraining member 28. The restraining member 28 comprises a shear pin (omitted for clarity), which shear pin may be engaged with a hole drilled through the work member 22, or (as shown) may act directly on the side of the piston. When the force on piston 6, due to expansion of the ignited fuel/air mixture, reaches a certain pre-determined level the shear pin shears, allowing the piston to be forced downwards at high velocity, driving the work member 22 into the medicament compartment 24. This in turn forces a narrow stream of the drug to be ejected at high velocity through the orifice 30 at the end of the drug delivery assembly and into the subject.

The injector assembly is provided with piston return means. In the illustrated embodiment, the return means comprises a return spring 32. Downward movement of the piston 6 compresses the return spring 32. Downward motion of the piston 6 is limited by the flanged portion 34 of the cylinder, and the action of the return spring 32 forces the piston to return to its uppermost, primed position. In other embodiments a more complicated return means, such as that disclosed in EP 0 316 468, may be employed. After the residual energy of the products of combustion has been dissipated, and after the piston 6 has returned to its primed position, exhaust valve 12 is opened (manually or automatically), silently venting the combustion products from the combustion chamber.

The fuel reservoir and fuel dosing components of the device will now be described in greater detail.

FIG. 1B shows a sectional view of one embodiment of a fuel reservoir for use in an injector device in accordance with the invention. The reservoir comprises a cylinder 40, a piston 42, and a cylinder head 44. The piston 42 comprises a circumferential groove 46 which accommodates an O ring (omitted for clarity) which forms a seal and which is resistant to liquefied butane or propane. Conveniently the O ring is formed from materials such as viton™, tygon™ or neoprene. A fuel storage chamber 48 is defined between the lower surface of the fuel reservoir piston 42 and the inner surfaces of the fuel reservoir cylinder 40. Fuel can be introduced into the storage chamber 48 by means of a fuel supply channel 50, a narrow longitudinal channel bored through the centre of the piston 42. The fuel supply channel 50 is provided with valve means to prevent the egress of fuel and seal the reservoir.

The chamber 48 is provided with a circular aperture, which acts as a fuel outlet 52. The outlet 52 is preferably provided with a valve means. Butane is the preferred fuel, but propane is also particularly suitable. The butane fuel is kept in liquid form at ambient temperature by the application of pressure above atmospheric. Substantially constant pressure is maintain on the fuel by a fuel reservoir spring (omitted for clarity), housed in a space between the cylinder head 44 and the upper surface of the piston 42, which tends to urge the piston 42 downwards, towards the fuel outlet 52. Conveniently a presure of about 7.5 bar is applied to the fuel in the chamber 48, which presure also serves to tend to force the fuel towards the fuel dosing assembly, shown in FIG. 1c.

Referring to FIG. 1c, a fuel dosing assembly comprises a housing 60 having a central bore 62, a circumferentially-grooved cylindrical plug 64 seated in the central bore 62 and movable therewithin, a fuel inlet 66, and a fuel outlet 68. The fuel dosing assembly is also provided with suitable fuel ducts 70, 72 to convey fuel from the reservoir to the dosing assembly, and from the dosing assembly to the injector assembly, respectively.

Figure 2B:
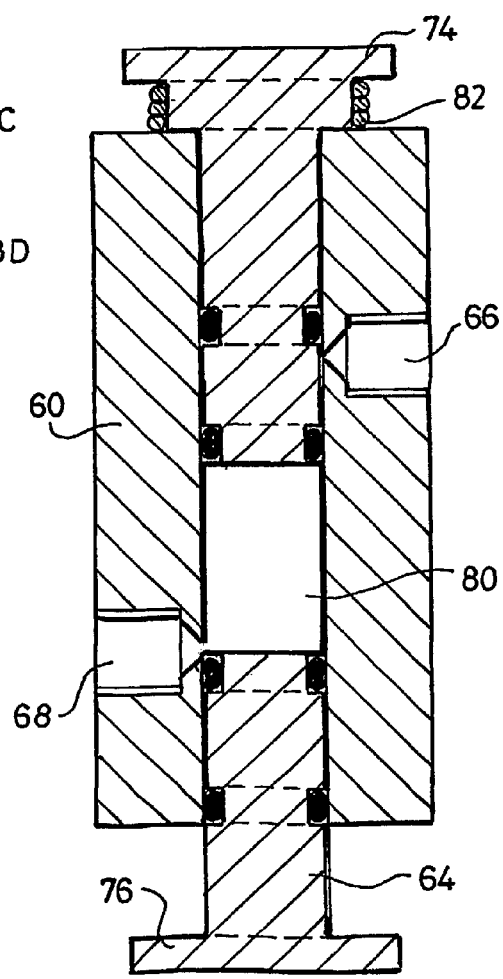

The fuel metering assembly is illustrated in greater detail in FIGS. 2A and 2B. Identical reference numerals are used in FIGS. 2A and 2B to denote the integers illustrated in FIG. 1C.

As is apparent from FIGS. 2A, B, the cylindrical plug 64 is provided with flanged portions 74, 76 at respective opposed ends, which serve to limit the axial displacement of the plug 64 within the housing 60. The plug 64 is provided with four circumferential grooves 78A, B, C and D, each of which accommodates an O ring formed of viton™, tygon™, neoprene or similar butane-resistant material, forming a seal between the plug 64 and the inner surface of the housing 60.

A dosing chamber 80 is located between the grooves 78B, C and their associated O rings. In the embodiment illustrated in FIGS. 2A, B, the dosing chamber 80 has a volume of about 1.6 microliter. Plug 64 is movable within the bore 62, between a charging position (shown in FIG. 2A) and a discharging position (shown in FIG. 2B). Biasing means, comprising spring 82, acts to urge the plug 64 into the charging position. Movement of the plug 64 from the charging position to the discharging position compresses spring 82. Accordingly when pressure (e.g. from a user's hand) is removed from top end of the plug 64, the spring 82 forces the plug 64 to return to the charging position.

When the plug 64 is in the charging position, liquefied butane fuel from the fuel reservoir is free to flow through fuel inlet 66 into the dosing chamber 80, until the chamber 80 is full. Downward movement of the plug 64 to the discharging position (FIG. 2B) seals off the fuel inlet 66, and allows the dosing chamber 80 to communicate with the fuel outlet 68, thereby discharging a predetermined dose of fuel to the fuel inlet of the combustion chamber. The combustion chamber is, initially, at atmospheric pressure, so the liquid fuel vapourises as it enters the combustion chamber.

Figure 3:
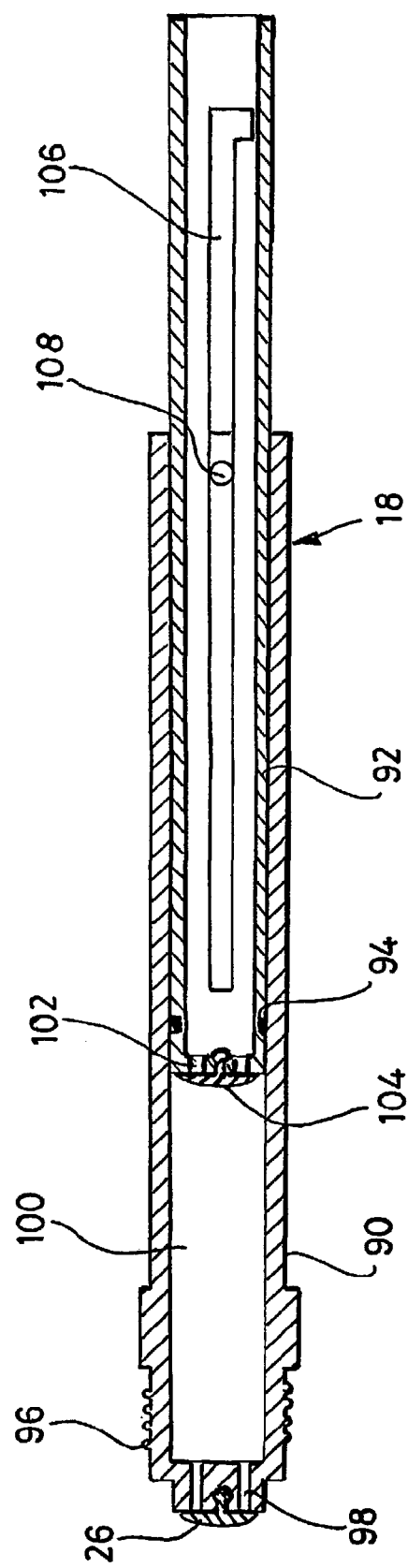
FIG. 3 is a sectional view on a different scale, of a priming means for use in a device in accordance with the invention.

The priming means, denoted by reference numeral 18 in FIG. 1A, will now be described in greater detail with reference to FIG. 3.

The priming means comprises a cylinder 90 and a hollow plunger 92 slidably mounted within the cylinder. The interior of the plunger is open to the atmosphere, and thus is filled with air at atmospheric pressure. A seal is effected between the cylinder 90 and plunger 92 by O ring 94, seated in a groove formed in the plunger 92. The cylinder 90 has a screw-threaded portion 96 disposed towards one end, which enters into screw-threaded engagement with the cylinder head (indicated by reference numeral 8 in FIG. 1A), and forming a seal therewith.

Accordingly the end portion of the cylinder 90 projects into the combustion chamber. An air inlet (denoted by reference numeral 14 in FIG. 1A) into the combustion chamber is provided by two apertures 98 bored in the end portion of the cylinder 90. The air inlet is sealable by a sealing means, which comprises an umbrella valve 26, formed of a resiliently deformable material, such as rubber, silicon, neoprene and the like. Suitable umbrella valves are obtainable from Vemay Europa B.V. (Oldenzaal, The Netherlands).

The end portion of the plunger 92 is similar in structure to the end portion of the cylinder 90. Accordingly, a priming chamber 100, defined between the cylinder 90 and the end of the plunger 92, is provided with an air inlet comprising two apertures 102 formed in the end of the plunger 92. The inlet is sealable by sealing means comprising umbrella valve 104, generally similar to valve 26.

A pair of L-shaped slots 106 are formed along the axis of the plunger 92. These engage with a pin 108, which passes through each slot and through an aperture provided in the wall of the cylinder 90. The engagement between the pin 108 and the slots 106 defines the extent of the travel of the plunger 92 within the cylinder 90. Accordingly, the plunger 92 may be moved between a position in which it is fully depressed, and a position in which it is fully withdrawn. FIG. 3 shows the priming means 18 when the plunger is at an intermediate position.

The operation of the priming means will now be described.

In order to prime the device, the plunger 92 is rotated through a small angle, to align the pin 108 with the slots 106.

The plunger may then be fully withdrawn to the end of its travel, until the pin 108 reaches the bottom of the slots 106. Withdrawal of the plunger 92 creates a partial vacuum within the priming chamber 100. This tends to distort the resiliently deformable material of the umbrella valve 104, opening the aperture 102 and thus allowing a pre-determined volume of air at atmospheric pressure to fill the priming chamber 100. During this time, the valve 28 remains closed, sealing apertures 98.

Subsequently depression of the plunger 92 tends to cause valve 104 to close and thus increase the pressure of the air in the priming chamber 102. The increased pressure in the chamber 102 in turn causes deformation of the resiliently deformable valve 26, which opens, allowing the air to enter the combustion chamber. Accordingly, depression of the plunger 92 to its fully depressed position causes a fixed volume of air to be transferred from the priming chamber 102 to the combustion chamber (which has a smaller volume) and thus be compressed by a pre-determined amount. These steps can be repeated to increase the amount of air and/or pressure thereof in the combustion chamber. When the plunger 92 is fully depressed, it can be rotated through a small angle, causing the pin 108 to enter the right-angled portion of the L-shaped slots 106, thereby locking the plunger 92 in position.

Upon firing of the device, the procedure may be repeated to re-prime the device and allow repeated firing, as desired.

It will be apparent that the above description relates only to an embodiment of the invention, and that the invention encompasses other embodiments as defined by the claims set out hereafter.

The invention claimed is:

1. A portable device for delivering a medicament or the like into the body of a human or animal subject, the device comprising: a medicament compartment containing the medicament or the like to be delivered; delivery means comprising an orifice through which the medicament or the like is expelled from the device; an internal combustion engine which provides the motive force by which the medicament is expelled from the device; a body comprising a cylinder, a piston located within the cylinder, and a cylinder head; a fuel reservoir, said reservoir comprising sufficient fuel to power a plurality of combustion cycles of the engine; a fuel inlet to admit fuel from the reservoir into the engine, and further comprising
   (i) means for causing compression of the fuel/combustion-supporting gas mixture within the combustion chamber;
   (ii) restraining means which serves to keep the piston in place against the pressure of the compressed fuel/combustion-supporting gas mixture, but which is insufficient to restrain the piston when the mixture is ignited; and
   (iii) a weak return means which is only just sufficient to overcome the inherent resistance of the piston when the device has been fired.

2. A device according to claim 1, comprising priming means to introduce an accurately pre-determined amount of combustion-supporting gas into the combustion chamber.

3. A device according to claim 2, wherein the priming means is adjustable to allow for introduction of variable, pre-determined amounts of combustion-supporting gas into the combustion chamber.

4. A device according to claim 2, wherein operation of the priming means also serves to pressurise the combustion-supporting gas within the combustion chamber.

5. A device according to claim 1 wherein operation of the device causes a work member operably linked to the piston to expel a dose of medicament from the device, and wherein the piston is allowed to accelerate before contacting the work member.

6. A device according to claim 5 wherein, when the device is primed and ready to operate, a small gap is provided between neighbouring end portions of the piston and the work member.

7. A device according to claim 1 comprising: a combustion chamber defined by the cylinder head, the cylinder and the piston, the combustion chamber being provided with means for forming a combustible mixture of fuel and combustion-supporting gas in the chamber and ignition means for igniting the mixture; and a work member operably linked, but not necessarily attached, to the piston.

8. A device according to claim 1, wherein the fuel inlet means comprises a fuel dosing assembly for metering a dose of fuel from a reservoir of liquefied gas fuel to be delivered to the combustion chamber, characterised in that the dose of liquefied gas fuel is accurately metered without undergoing a phase change.

9. A device according to claim 1, further comprising an exhaust valve for venting the products of combustion from the combustion chamber, characterised in that the exhaust valve opens only after the combustion has been completed and all movement of the piston ceased.

10. A device according to claim 1 wherein the combustion-supporting gas is air.

11. A device according to claim 1, comprising a fuel dosing assembly which is adjustable to meter variable, accurately predetermined doses of fuel.

12. A device according to claim 1, wherein the fuel reservoir contains liquefied gas fuel which is maintained in a liquid state in the reservoir by active pressurising means.

13. A device according to claim 1, comprising trigger means which, when actuated, will cause the device to perform a single combustive event.

14. A device according to claim 1, wherein the medicament compartment is a readily removable component, so as to allow replacement or replenishment when the medicament has been exhausted.

15. A device according to claim 1 in the form of a needleless injector.

16. A device according to claim 1 wherein, upon operation, medicament is expelled through the orifice at a velocity in the range 50-150 m/s.

* * * * *